United States Patent

Matsuda et al.

[11] Patent Number: 5,977,148
[45] Date of Patent: Nov. 2, 1999

[54] TERMITICIDE

[75] Inventors: Michihiko Matsuda, Odawara; Renpei Hatano; Makio Yano, both of Shizuoka, all of Japan

[73] Assignee: Nipppon Soda Co., Ltd., Tokyo, Japan

[21] Appl. No.: 09/007,489

[22] Filed: Jan. 15, 1998

Related U.S. Application Data

[63] Continuation-in-part of application No. 08/351,358, Apr. 11, 1995, abandoned.
[51] Int. Cl.$^6$ .......................... A01N 43/40; A01N 43/60; A01N 43/78; A01N 43/80
[52] U.S. Cl. .......................... 514/357; 514/255; 514/365; 514/372
[58] Field of Search .................................. 514/255, 357, 514/365, 372

[56] References Cited

U.S. PATENT DOCUMENTS

| | | | |
|---|---|---|---|
| 5,087,632 | 2/1992 | Tsuboi et al. | 514/357 |
| 5,196,442 | 3/1993 | Tsuboi et al. | 514/357 |

FOREIGN PATENT DOCUMENTS

| | | |
|---|---|---|
| WO 91/4965 | 4/1991 | WIPO . |
| WO 92/21241 | 12/1992 | WIPO . |

OTHER PUBLICATIONS

Worthing et al, "The Pesticide Manual" (1991) pp. 166 & 167.

*Primary Examiner*—Allen J. Robinson
*Attorney, Agent, or Firm*—Joseph C. Mason, Jr.; Mason & Assoc., P.A.

[57] ABSTRACT

A termiticidal composition containing a compound represented by the formula [I];

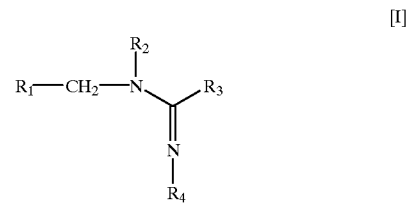

wherein $R_1$ represents 2-chloro-5-pyridyl, 2-chloro-5-pyrazinyl, 2-methyl-5-pyrazinyl or 2-chloro-5-thiazolyl; $R_2$ represents hydrogen, methyl, ethyl, methoxymethyl, cyclopropyl, propynyl or methoxy; $R_3$ represents hydrogen or methyl or chloromethyl; and $R_4$ represents cyano or nitro, or a salt thereof as an active ingredient.

2 Claims, No Drawings

TERMITICIDE

This application is a continuation-in-part application to Ser. No. 08/351,358, filed Apr. 11, 1995, now abandoned.

TECHNICAL FIELD

The present invention relates to a termiticide comprising a amine derivative represented by the formula [I] as shown below or a salt thereof as the active ingredient.

BACKGROUND ART

Many types of termiticide, such as organochlorine compounds, organophosphorous compounds, carbamate compounds, etc., have been used for the control of termites in the past, however, most of those termiticide have not been always satisfied in terms of their insufficient effectiveness and/or their high toxic property. Therefore, the development of novel termiticide which has less disadvantages as described above and is highly safe to human beings, has been intensively demanded.

The compounds, the manufacturing process and the use of those amine derivatives of present invention as insecticides are disclosed in WO91/04965 (U.S. Pat. No. 5,304,566 and 5,612,358).

It is described that a kind of 2-chloro-5-pyridylmethylamino derivatives have termiticidal effect in U.S. Pat. No. 5,196,442.

DISCLOSURE OF INVENTION

The object of the present invention is to provide a termiticide having strong activity, firm effectiveness and capable of using it safely. The present invention is a termiticide containing at least either a compound represented by the formula [I];

$$R_1-CH_2-N(R_2)-C(R_3)=N-R_4 \quad [I]$$

wherein $R_1$ represents 2-chloro-5-pyridyl, 2-chloro-5-pyrazinyl, 2-methyl-5-pyrazinyl or 2-chloro-5-thiazolyl; $R_2$ represents hydrogen, methyl, ethyl, methoxymethyl, cyclopropyl, propynyl or methoxy; $R_3$ represents hydrogen or methyl or chloromethyl; and $R_4$ represents cyano or nitro, or a salt thereof as an active ingredient.

For the examples of the amine derivatives of the invention represented by the formula [I], there are recited several compounds in Table 1. The manufacturing process of the amine derivatives represented by the formula [I] and the salts thereof is disclosed in WO91/04965.

TABLE 1

Chemical Structure $$R_1-CH_2-N(R_2)-C(R_3)=N-R_4$$

| Compound No. | $R_1$ | $R_2$ | $R_3$ | $R_4$ | Physical Constant [ ]Melting Point ° C. |
|---|---|---|---|---|---|
| 1 | 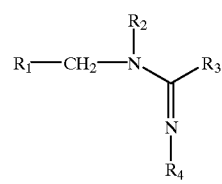 | H | $CH_3$ | CN | [141–143] |
| 2 | " | $CH_3$ | " | " | [101–103] |
| 3 | " | " | $CH_2Cl$ | " | $N_D^{26.5}$ 1.5921 |
| 4 | " | $C_2H_5$ | $CH_3$ | " | [100–101] |
| 5 | " | $CH_2OCH_3$ | " | " | $N_D^{25.5}$ 1.5711 |
| 6 | " | $CH_2C\equiv CH$ | " | " | $N_D^{25.5}$ 1.5730 |
| 7 | " | $OCH_3$ | " | " | [110–112] |
| 8 | " | ◁ | " | " | [73–75] |
| 9 | " | $CH_3$ | H | " | [167–170] |
| 10 | " | " | $CH_3$ | $NO_2$ | $N_D^{25}$ 1.5808 |
| 11 | Cl-pyrazinyl | $CH_3$ | $CH_3$ | CN | [94–96] |

TABLE 1-continued

Chemical Structure $$R_1-CH_2-\underset{\underset{R_4}{\overset{\|}{N}}}{\overset{R_2}{\underset{|}{N}}}\diagdown R_3$$

| Compound No. | $R_1$ | $R_2$ | $R_3$ | $R_4$ | Physical Constant [ ]Melting Point ° C. |
|---|---|---|---|---|---|
| 12 | (2-chloro-5-methylthiazol-yl) | " | " | " | [143–144] |
| 13 | (2-methyl-5-pyrazinyl) | " | " | " | $N_D^{25}$ 1.5612 |

It is possible to control Isopterous insects such as termites, including *Coptotermes formosanus* Shiraki, *Reticulitermes speratus* Kolbe, *Cryptotermes domesticus* Haviland, *Incisitermes minor* Hagen, *Odontotermes formosanus* Shiraki, etc. by applying the amine derivative represented by the formula [I] or the salt thereof against such termites.

The termiticide according to the present invention comprises a compound represented by the formula [I] or the salt thereof as the active ingredient. The compound as the active ingredient can be applied without being subject to the formulation, however, it is normally used in the typical applicable form for this sort of agents, such as wettable powder, water soluble powder, dust formulation, emulsifiable concentrate, liquid, granular formulation, flowable formulation, paste, aerosol, fumigant and smoking generator. For additives and carriers, if solid formulations are required, plant-origin powder such as soybean powder and wheat flour, fine mineral powder such as diatomaceous earth, apatite, gypsum, talc, bentonite, clay, etc., and organic or inorganic compounds, such as sodium benzoate, urea and Glauber's salt can be used.

For liquid formulations, vegetable oils, mineral oils, distillate fractions of petroleum such as kerosene, xylene and solvent naphtha, cyclohexane, cyclohexanone, dimethylformamide, dimethylsulfoxide, trichloroethylene, methyl isobutyl ketone, water, etc. can be used as a solvent. In order to attain homogeneous and stable dilution, surfactant may be added, if required. The wettable powders, emulsifiable concentrates, water soluble powders and flowable formulations thus obtained may be sprayed after diluting them up to a desired concentration in suspension, solution or emulsion, while the dust and granular formulations may be sprayed directly.

The concentration of the active ingredient in the formulation and the dosage of the formulation to be applied may be determined adequately according to each of the type of formulation, application method and the objective variety of termites.

The content of the compound represented by the general formula [I] or the salt thereof as the active ingredient in the formulation is normally prepared in a range from 0.1 to 40% by weight, preferably from 1 to 30% by weight.

The termiticide according to the present invention can be applied in formulated or non-formulated form in such ways as coating, blowing, spraying, dipping, injecting under pressure, kneading, mixing, etc. to the termite-outbreaking sites and nests of termites, building materials such as foundations and posts, buildings, soil surrounding buildings, concrete blocks, floor slabs, coat materials for electric wires and various kinds of cables.

Despite single application of the compound represented by the formula [I] or the salt thereof is sufficiently effective against termites, such compounds and their salts can be applied in combination with synergistic agent such as S-421 and piperonyl butoxide, insecticides, acaricides, fungicides and/or antiseptics.

Representative insecticides, acaricides, fungicides and antiseptics which can be used in combination with the compound specified in the present invention include the followings.

Organophosphorous and Carbamate Insecticides

Fenthion, fenitrothion, diazinon, chlorpyriphos, ESP, vamidothion, fenthoate, dimethoate, formothion, malathion, trichlorfon, thiometon, phosmet, diclorvos, acephate, EPBP, methyl parathion, oxydimethon methyl, ethion, salithion, cyanophos, isoxathion, pyridafenthion, phosalone, methidathion, sulprophos, pyrachlophos, monocrotophos, fenamiphos, aldicarb, propoxur, methomyl, BPMC, MTMC, carbaryl, cartap, thiocyclam, bensultap, carbosulfan, benfuracarb, pyrimicarb, ethiofencarb, phenoxycarb, and thiodicarb.

Pyrethroid Insecticides

Permethrin, cypermethrin, deltamethrin, fenvalerate, fenpropathrin, pyrethrin, allethrin, tetramethrin, resmethrin, dimethrin, propathrin, bifenthrin, prothrin, fluvalinate, cyfluthrin, cyhalothrin, flucythrinate, ethofenprox, cycloprothrin, tralomethrin, and silafluophane.

Benzoylphenylureas and Other Insecticides

Diflubenzuron, chlorfluazuron, triflumuron, teflubenzuron, hexaflumuron, triflumuron, flufenoxuron, buprofezin, pyriproxifen, diafenthiuron, machine oil, nicotine sulfate, and *Bacillus thuringensis*.

Acaricides (Fungicides)

Chlorobenzilate, fenithobromolate, dicofol, chlordimeform, amitraz, BPPS, benzomate, hexythiazox, fenbutatin oxide, polynactin, quinomethionate, CPCBS, tetradifon, avermectin, polysulfide lime, clofentezin, flubenzamin, flufenoxuron, cyhexatin, pyridaben, fenpyroximate, tebufenpyrad, thiaphanate methyl, benomyl, thiuram, IBP, EDDP, fthalide, probenazole, isoprothiolane, TPN, captan, polyoxin, blastcidin-S, kasugamycin, validamycin, tricyclazole, pyroquilon, phenazine oxide, mepronil, flutolanil, pencycron, iprodione, hymexazol, metalaxil, triflumizol, diclomezin, teclofthalam, propineb, ziram, dithianone, fosetyl, triforine, vinclozolin, procymidon, oxadixyl, triadimefon, bitertanol, fenarimol, guazatin, propamocarb hydrochloride, and fluazinam.

Antiseptics

Pentachlorophenyl laurate, p-bromo-2,6-dichlorophenol, 3-iodo-2-propinylbutylcarbamate, 3-ethoxycarbonyloxy-1-bromo-1,2-diiodopropene, benzalconium chloride, dialkyl dimethylammonium chloride, bis(n-tributyltin)oxide, tributyltin telefthalate, zinc aphtenate and xyligen alminium salt.

BEST MODE FOR CARRYING OUT THE INVENTION

Now, the examples of the formulation containing the inventive compound are described hereinbelow, however, carriers and surfactants to be combined thereto shall not be limited to the ones described in the following examples.

EXAMPLE 1

Emulsifiable Concentrate

| | |
|---|---|
| Compound represented by the formula [I] or the salt thereof | 10 parts by weight |
| Alkylphenyl polyoxyethylene | 5 parts by weight |
| Dimethyl formamide | 50 parts by weight |
| Xylene | 35 parts by weight |

All of the above components are mixed and dissolved to obtain an emulsifiable concentrate, which is then prepared to emulsion by diluting it with water at the use and sprayed.

EXAMPLE 2

Wettable Powder

| | |
|---|---|
| Compound represented by the formula [I] or the salt thereof | 20 parts by weight |
| Sulfuric acid ester of higher alcohol | 5 parts by weight |
| Diatomaceous earth | 70 parts by weight |
| Silica | 5 parts hy weight |

All of the above components are mixed and micronized to obtain the fine powder, which is then prepared to suspension by diluting it with water at the use and sprayed.

EXAMPLE 3

Dust Formulation

| | |
|---|---|
| Compound represented by the formula [I] or the salt thereof | 5 parts by weight |
| Talc | 94.7 parts by weight |
| Silica | 0.3 parts by weight |

All of the above components are mixed and pulverized to obtain dusting powder, which is then applied directly at the use.

EXAMPLE 4

Granular Formulation

| | |
|---|---|
| Compound represented by the formula [I] or the salt thereof | 5 parts by weight |

-continued

| | |
|---|---|
| Clay | 73 parts by weight |
| Bentonite | 20 parts by weight |
| Sodium dioctylsulfosuccinate | 1 part by weight |
| Sodium phosphate | 1 part by weight |

All of the above components are granulated to obtain a granular formulation, which is then applied directly at the use.

INDUSTRIAL APPLICABILITY

Test Example 1

The emulsifiable concentrate according to the example 1 is diluted with acetone, then 1 ml of the solution was fed dropwise onto a filter paper placed in a glass petridish having a diameter of 9 cm. After drying naturally, 10 worker *Coptotermes formosanus* Shiraki were put in the petridish, and the petridish was closed with a cover and placed in an incubator maintained at 25° C. Two days later, the number of dead termites was counted and mortality was calculated. The results is summarized in Table 2.

TABLE 2

| Compound No. | Dose of Active Ingredient (mg/m$^2$) | Mortality (%) |
|---|---|---|
| 2 | 500 | 100 |
| 8 | 500 | 100 |
| 12 | 500 | 100 |
| Check | 0 | 0 |

Test Example 2

Test solutions were prepared by dissolving in dimethyl formamide containing 1.5% Tween 20 to prepare a 5% stock solution. Each of the stock solutions was diluted to the appropriate concentration by the addition of water.

One ml the aqueous solution prepared in the above mentioned procedure was uniformly applied to a piece of filter paper using a pipette. The treated filter paper was then placed in a 8 mm diameter plastic cup. Ten workers of *Reticulitermes speratus* were replaced in the plastic cup and incubated at 25° C. and 65% relative humidity. The % knock down and mortality were then determined after 3 hours and 4 days, respectively, after treatment. The test procedure was repeated in duplicate. The result are shown in the following table.

TABLE 3

| Compound No. | Concentration (ppm) | % knock down 3 HAT[1)] | mortality(moribund) 4 DAT[2)] |
|---|---|---|---|
| 2 | 500 | 100 | 100 |
| | 125 | 100 | 100 |
| | 31.3 | 100 | 100 |
| | 7.8 | 100 | 100 |
| | 1.95 | 100 | 100 |
| | 0.49 | 100 | 100 |
| | 0.12 | 100 | 20 |
| | 0.03 | 0 | 0 |
| Comparative Compound A*[1] | 500 | 100 | 100 |
| | 125 | 100 | 100 |
| | 31.3 | 100 | 100 |
| | 7.8 | 90 | 90 |
| | 1.95 | 100 | 40(10) |
| | 0.49 | 100 | 20 |
| | 0.12 | 0 | 0 |
| | 0.03 | 0 | 0 |

TABLE 3-continued

| Compound No. | Concentration (ppm) | % knock down 3 HAT[1] | mortality(moribund) 4 DAT[2] |
|---|---|---|---|
| Comparative Compound B*[2] | 500 | 80 | 100 |
| | 125 | 100 | 50(40) |
| | 31.3 | 70 | 20(60) |
| | 7.8 | 100 | 50(10) |
| | 1.95 | 60 | 30(10) |
| | 0.49 | 0 | 0 |
| | 0.12 | 0 | 0 |
| | 0.03 | 0 | 0 |

[1]HAT: hours after treatment,
[2]DAT: days after treatment
*[1]Comparative Compound A

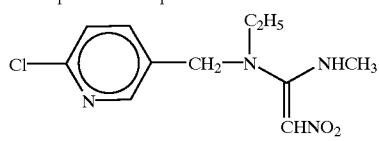

nitenpyram (compound described in U.S. Pat. No. 5,196,442)
*[2]Comparative Compound B

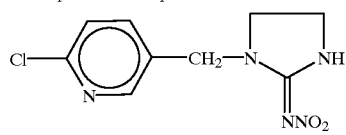

imidacloprid (commercial termiticide)

What is claimed is:

1. A method for exterminating termites of the order Isoptera comprising contacting said termites or a locus from which it is desired to exclude said termites with a termiticide in a concentration of not more than 0.12 ppm of an active ingredient which consists essentially of a compound represented by the formula (I).

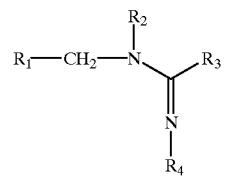

wherein $R_1$ represents 2-chloro-5-pyridyl, 2-chloro-5-pyrazinyl, 2-methyl-5-pyrazinyl or 2-chloro-5-thiazolyl; $R_2$ represents hydrogen, methyl, ethyl, methoxymethyl, cyclopropyl, propynyl, or methoxy, $R_3$ represents hydrogen or methyl or chloromethyl; and $R_4$ represents cyano or nitro; or a salt thereof.

2. The method according to claim 1, wherein $R_1$ represents 2-chloro-5-pyridyl; $R_2$ represents methyl; $R_3$ represents methyl; and $R_4$ represents cyano.

* * * * *

UNITED STATES PATENT AND TRADEMARK OFFICE
CERTIFICATE OF CORRECTION

PATENT NO : 5,977,148

DATED : November 2, 1999

INVENTOR(S) : Michihiko Matsuda, Renpei Hatano and Makio Yano

It is certified that error appears in the above-identified patent and that said Letters Patent is hereby corrected as shown below:

Col. 4, line 36
 replace "Carbamate Insecticides"
 with --Carbamate Insecticides; --.

Col. 4, line 46
 replace "Pyrethroid Insecticides"
 with --Pyrethroid Insecticides; --.

Col. 4, line 53
 replace "Other Insecticides"
 with --Other Insecticides; --.

Col. 4, line 57
 replace "Acaricides (Fungicides)"
 with --Acaricides (Fungicides); --.

Col. 5, line 4
 replace "Antiseptics"
 with --Antiseptics; --.

Col. 5, line 40
 replace "Silica    5 parts hy weight"
 with --Silica    5 parts by weight --.

Signed and Sealed this

Thirtieth Day of May, 2000

Attest:

*Attesting Officer*

Q. TODD DICKINSON

*Director of Patents and Trademarks*